US008071935B2

(12) United States Patent
Besko et al.

(10) Patent No.: US 8,071,935 B2
(45) Date of Patent: Dec. 6, 2011

(54) OPTICAL DETECTOR WITH AN OVERMOLDED FARADAY SHIELD

(75) Inventors: David P. Besko, Thornton, CO (US); Daniel J. Peters, Longmont, CO (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 531 days.

(21) Appl. No.: 12/165,052

(22) Filed: Jun. 30, 2008

(65) Prior Publication Data

US 2009/0323267 A1   Dec. 31, 2009

(51) Int. Cl.
*H01J 27/14* (2006.01)
*H05K 9/00* (2006.01)

(52) U.S. Cl. .......................... 250/239; 361/818; 361/820

(58) Field of Classification Search .................. 250/239; 361/816, 818, 820; 257/434, 659, 790
See application file for complete search history.

(56) References Cited

U.S. PATENT DOCUMENTS

| | | | |
|---|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |

(Continued)

FOREIGN PATENT DOCUMENTS

DE   3516338   11/1986

(Continued)

OTHER PUBLICATIONS

Faisst, Karin, et al.; "Intrapartum Reflectance Pulse Oximetry: Effects of Sensor Location and Fixation Duration on Oxygen Saturation Readings," Journal of Clinical Monitoring, vol. 13, pp. 299-302 (1997).

(Continued)

*Primary Examiner* — John Lee
(74) *Attorney, Agent, or Firm* — Fletcher Yoder

(57) ABSTRACT

Embodiments described herein may include devices and methods of manufacturing devices for sensing and monitoring physiological parameters of a patient. Specifically, certain embodiments disclose the use of conductive and nonconductive overmold materials to protect the device, increase reliability, increase comfort, and increase accuracy of the parameters measured.

17 Claims, 6 Drawing Sheets

U.S. PATENT DOCUMENTS

| | | |
|---|---|---|
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,039 A * | 8/1991 | Hattori et al. ............... 257/463 |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |

| Patent No. | Date | Inventor(s) |
|---|---|---|
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,594,204 A * | 1/1997 | Taylor et al. .................. 174/527 |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,626,140 A | 5/1997 | Feldman et al. |
| 5,629,992 A * | 5/1997 | Amersfoort et al. ............ 385/15 |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,060 A | 7/1997 | Yorkey et al. |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,677,511 A * | 10/1997 | Taylor et al. .................. 174/527 |
| 5,678,544 A | 10/1997 | DeLonzor et al. |
| 5,679,975 A * | 10/1997 | Wyland et al. ................ 257/659 |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |

| | | |
|---|---|---|
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |
| 6,081,742 A | 6/2000 | Amano et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllerman et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |

| | | | | | | |
|---|---|---|---|---|---|---|
| 6,463,311 B1 | 10/2002 | Diab | | 6,671,531 B2 | 12/2003 | Al-Ali et al. |
| 6,466,808 B1 | 10/2002 | Chin et al. | | 6,671,532 B2 | 12/2003 | Fudge et al. |
| 6,466,809 B1 | 10/2002 | Riley | | 6,675,031 B1 | 1/2004 | Porges et al. |
| 6,470,199 B1 | 10/2002 | Kopotic et al. | | 6,678,543 B2 | 1/2004 | Diab et al. |
| 6,470,200 B2 | 10/2002 | Walker et al. | | 6,681,126 B2 | 1/2004 | Solenberger |
| 6,480,729 B2 | 11/2002 | Stone | | 6,681,128 B2 | 1/2004 | Steuer et al. |
| 6,490,466 B1 | 12/2002 | Fein et al. | | 6,681,454 B2 | 1/2004 | Modgil et al. |
| 6,496,711 B1 | 12/2002 | Athan et al. | | 6,684,090 B2 | 1/2004 | Ali et al. |
| 6,498,942 B1 | 12/2002 | Esenaliev et al. | | 6,684,091 B2 | 1/2004 | Parker |
| 6,501,974 B2 | 12/2002 | Huiku | | 6,694,160 B2 | 2/2004 | Chin |
| 6,501,975 B2 | 12/2002 | Diab et al. | | 6,697,653 B2 | 2/2004 | Hanna |
| 6,505,060 B1 | 1/2003 | Norris | | 6,697,655 B2 | 2/2004 | Sueppel et al. |
| 6,505,061 B2 | 1/2003 | Larson | | 6,697,656 B1 | 2/2004 | Al-Ali |
| 6,505,133 B1 | 1/2003 | Hanna et al. | | 6,697,658 B2 | 2/2004 | Al-Ali |
| 6,510,329 B2 | 1/2003 | Heckel | | RE38,476 E | 3/2004 | Diab et al. |
| 6,510,331 B1 | 1/2003 | Williams et al. | | 6,699,194 B1 | 3/2004 | Diab et al. |
| 6,512,937 B2 | 1/2003 | Blank et al. | | 6,699,199 B2 | 3/2004 | Asada et al. |
| 6,515,273 B2 | 2/2003 | Al-Ali | | 6,701,170 B2 | 3/2004 | Stetson |
| 6,519,484 B1 | 2/2003 | Lovejoy et al. | | 6,702,752 B2 | 3/2004 | Dekker |
| 6,519,486 B1 | 2/2003 | Edgar, Jr. et al. | | 6,707,257 B2 | 3/2004 | Norris |
| 6,519,487 B1 | 2/2003 | Parker | | 6,708,049 B1 | 3/2004 | Berson et al. |
| 6,525,386 B1 | 2/2003 | Mills et al. | | 6,709,402 B2 | 3/2004 | Dekker |
| 6,526,300 B1 | 2/2003 | Kiani et al. | | 6,711,424 B1 | 3/2004 | Fine et al. |
| 6,526,301 B2 | 2/2003 | Larsen et al. | | 6,711,425 B1 | 3/2004 | Reuss |
| 6,541,756 B2 | 4/2003 | Schulz et al. | | 6,714,803 B1 | 3/2004 | Mortz |
| 6,542,764 B1 | 4/2003 | Al-Ali et al. | | 6,714,804 B2 | 3/2004 | Al-Ali et al. |
| 6,546,267 B1 | 4/2003 | Sugiura et al. | | 6,714,805 B2 | 3/2004 | Jeon et al. |
| 6,553,241 B2 | 4/2003 | Mannheimer et al. | | RE38,492 E * | 4/2004 | Diab et al. .................. 600/364 |
| 6,553,242 B1 | 4/2003 | Sarussi | | 6,719,686 B2 | 4/2004 | Coakley et al. |
| 6,553,243 B1 | 4/2003 | Gurley | | 6,719,705 B2 | 4/2004 | Mills |
| 6,556,852 B1 | 4/2003 | Schulze et al. | | 6,720,734 B2 | 4/2004 | Norris |
| 6,560,470 B1 | 5/2003 | Pologe | | 6,721,584 B2 | 4/2004 | Baker, Jr. et al. |
| 6,564,077 B2 | 5/2003 | Mortara | | 6,721,585 B1 | 4/2004 | Parker |
| 6,564,088 B1 | 5/2003 | Soller et al. | | 6,725,074 B1 | 4/2004 | Kästle |
| 6,571,113 B1 | 5/2003 | Fein et al. | | 6,725,075 B2 | 4/2004 | Al-Ali |
| 6,571,114 B1 | 5/2003 | Koike et al. | | 6,731,963 B2 | 5/2004 | Finarov et al. |
| 6,574,491 B2 | 6/2003 | Elghazzawi | | 6,731,967 B1 | 5/2004 | Turcott |
| 6,580,086 B1 | 6/2003 | Schulz et al. | | 6,735,459 B2 | 5/2004 | Parker |
| 6,584,336 B1 | 6/2003 | Ali et al. | | 6,745,060 B2 | 6/2004 | Diab et al. |
| 6,587,703 B2 | 7/2003 | Cheng et al. | | 6,745,061 B1 | 6/2004 | Hicks et al. |
| 6,587,704 B1 | 7/2003 | Fine et al. | | 6,748,253 B2 | 6/2004 | Norris et al. |
| 6,589,172 B2 | 7/2003 | Williams et al. | | 6,748,254 B2 | 6/2004 | O'Neill et al. |
| 6,591,122 B2 | 7/2003 | Schmitt | | 6,754,515 B1 | 6/2004 | Pologe |
| 6,591,123 B2 | 7/2003 | Fein et al. | | 6,754,516 B2 | 6/2004 | Mannheimer |
| 6,592,986 B1 * | 7/2003 | Hakotani et al. .............. 428/332 | | 6,760,607 B2 | 7/2004 | Al-Ali |
| 6,594,511 B2 | 7/2003 | Stone et al. | | 6,760,609 B2 | 7/2004 | Jacques |
| 6,594,512 B2 | 7/2003 | Huang | | 6,760,610 B2 | 7/2004 | Tscupp et al. |
| 6,594,513 B1 | 7/2003 | Jobsis et al. | | 6,763,255 B2 | 7/2004 | DeLonzor et al. |
| 6,597,931 B1 | 7/2003 | Cheng et al. | | 6,763,256 B2 | 7/2004 | Kimball et al. |
| 6,597,933 B2 | 7/2003 | Kiani et al. | | 6,770,028 B1 | 8/2004 | Ali et al. |
| 6,600,940 B1 | 7/2003 | Fein et al. | | 6,771,994 B2 | 8/2004 | Kiani et al. |
| 6,606,510 B2 | 8/2003 | Swedlow et al. | | 6,773,397 B2 | 8/2004 | Kelly |
| 6,606,511 B1 | 8/2003 | Ali et al. | | 6,778,923 B2 | 8/2004 | Norris et al. |
| 6,606,512 B2 | 8/2003 | Muz et al. | | 6,780,158 B2 | 8/2004 | Yarita |
| 6,615,064 B1 | 9/2003 | Aldrich | | 6,792,300 B1 | 9/2004 | Diab et al. |
| 6,615,065 B1 | 9/2003 | Barrett et al. | | 6,793,654 B2 | 9/2004 | Lemberg |
| 6,618,602 B2 | 9/2003 | Levin et al. | | 6,801,797 B2 | 10/2004 | Mannheimer et al. |
| 6,622,034 B1 | 9/2003 | Gorski et al. | | 6,801,798 B2 | 10/2004 | Geddes et al. |
| 6,628,975 B1 | 9/2003 | Fein et al. | | 6,801,799 B2 | 10/2004 | Mendelson |
| 6,631,281 B1 | 10/2003 | Kästle | | 6,801,802 B2 | 10/2004 | Sitzman et al. |
| 6,643,530 B2 | 11/2003 | Diab et al. | | 6,802,812 B1 | 10/2004 | Walker et al. |
| 6,643,531 B1 | 11/2003 | Katarow | | 6,805,673 B2 | 10/2004 | Dekker |
| 6,647,279 B2 | 11/2003 | Pologe | | 6,810,277 B2 | 10/2004 | Edgar, Jr. et al. |
| 6,647,280 B2 | 11/2003 | Bahr et al. | | 6,813,511 B2 | 11/2004 | Diab et al. |
| 6,650,917 B2 | 11/2003 | Diab et al. | | 6,816,741 B2 | 11/2004 | Diab |
| 6,650,918 B2 | 11/2003 | Terry | | 6,819,950 B2 | 11/2004 | Mills |
| 6,654,621 B2 | 11/2003 | Palatnik et al. | | 6,822,564 B2 | 11/2004 | Al-Ali |
| 6,654,622 B1 | 11/2003 | Eberhard et al. | | 6,825,619 B2 | 11/2004 | Norris |
| 6,654,623 B1 | 11/2003 | Kästle | | 6,826,419 B2 | 11/2004 | Diab et al. |
| 6,654,624 B2 | 11/2003 | Diab et al. | | 6,829,496 B2 | 12/2004 | Nagai et al. |
| 6,658,276 B2 | 12/2003 | Kianl et al. | | 6,830,711 B2 | 12/2004 | Mills et al. |
| 6,658,277 B2 | 12/2003 | Wassermann | | 6,836,679 B2 | 12/2004 | Baker, Jr. et al. |
| 6,662,033 B2 | 12/2003 | Casciani et al. | | 6,839,579 B1 | 1/2005 | Chin |
| 6,665,551 B1 | 12/2003 | Suzuki | | 6,839,580 B2 | 1/2005 | Zonios et al. |
| 6,668,182 B2 | 12/2003 | Hubelbank | | 6,839,582 B2 | 1/2005 | Heckel |
| 6,668,183 B2 | 12/2003 | Hicks et al. | | 6,839,659 B2 | 1/2005 | Tarassenko et al. |
| 6,671,526 B1 | 12/2003 | Aoyagi et al. | | 6,842,635 B1 | 1/2005 | Parker |
| 6,671,528 B2 | 12/2003 | Steuer et al. | | 6,845,256 B2 | 1/2005 | Chin et al. |
| 6,671,530 B2 | 12/2003 | Chung et al. | | 6,850,787 B2 | 2/2005 | Weber et al. |

| Patent No. | Date | Name | | Patent No. | Date | Name |
|---|---|---|---|---|---|---|
| 6,850,788 B2 | 2/2005 | Al-Ali | | 7,280,858 B2 | 10/2007 | Al-Ali et al. |
| 6,850,789 B2 | 2/2005 | Schweitzer, Jr. et al. | | 7,295,866 B2 | 11/2007 | Al-Ali et al. |
| 6,861,639 B2 | 3/2005 | Al-Ali | | 7,305,262 B2 | 12/2007 | Brodnick et al. |
| 6,863,652 B2 | 3/2005 | Huang et al. | | 7,315,753 B2 | 1/2008 | Baker, Jr. et al. |
| 6,865,407 B2 | 3/2005 | Kimball et al. | | 7,648,858 B2 * | 1/2010 | Tang et al. ......... 438/124 |
| 6,879,850 B2 | 4/2005 | Kimball | | 7,741,567 B2 * | 6/2010 | Beddingfield et al. ........ 174/386 |
| 6,882,874 B2 | 4/2005 | Huiku | | 2001/0021803 A1 | 9/2001 | Blank et al. |
| 6,889,153 B2 | 5/2005 | Dietiker | | 2001/0051767 A1 | 12/2001 | Williams et al. |
| 6,898,452 B2 | 5/2005 | Al-Ali et al. | | 2002/0026109 A1 | 2/2002 | Diab et al. |
| 6,909,912 B2 | 6/2005 | Melker et al. | | 2002/0028990 A1 | 3/2002 | Shepherd et al. |
| 6,912,413 B2 | 6/2005 | Rantala et al. | | 2002/0038078 A1 | 3/2002 | Ito |
| 6,916,289 B2 | 7/2005 | Schnall | | 2002/0042558 A1 | 4/2002 | Mendelson |
| 6,920,345 B2 | 7/2005 | Al-Ali et al. | | 2002/0068859 A1 | 6/2002 | Knopp |
| 6,931,269 B2 | 8/2005 | Terry | | 2002/0128544 A1 | 9/2002 | Diab et al. |
| 6,934,570 B2 | 8/2005 | Kiani et al. | | 2002/0133067 A1 | 9/2002 | Jackson, III |
| 6,939,307 B1 | 9/2005 | Dunlop | | 2002/0156354 A1 | 10/2002 | Larson |
| 6,941,162 B2 | 9/2005 | Fudge et al. | | 2002/0173706 A1 | 11/2002 | Takatani |
| 6,947,781 B2 | 9/2005 | Asada et al. | | 2002/0173709 A1 | 11/2002 | Fine et al. |
| 6,950,687 B2 | 9/2005 | Al-Ali | | 2002/0190863 A1 | 12/2002 | Lynn |
| 6,963,767 B2 | 11/2005 | Rantala et al. | | 2002/0198442 A1 | 12/2002 | Rantala et al. |
| 6,971,580 B2 | 12/2005 | DeLonzor et al. | | 2003/0002271 A1 * | 1/2003 | Nurminen ............... 361/818 |
| 6,983,178 B2 | 1/2006 | Fine et al. | | 2003/0018243 A1 | 1/2003 | Gerhardt et al. |
| 6,985,763 B2 | 1/2006 | Boas et al. | | 2003/0036690 A1 | 2/2003 | Geddes et al. |
| 6,985,764 B2 | 1/2006 | Mason et al. | | 2003/0045785 A1 | 3/2003 | Diab et al. |
| 6,990,426 B2 | 1/2006 | Yoon et al. | | 2003/0073889 A1 | 4/2003 | Keilbach et al. |
| 6,992,751 B2 | 1/2006 | Al-Ali | | 2003/0073890 A1 | 4/2003 | Hanna |
| 6,992,772 B2 | 1/2006 | Block et al. | | 2003/0100840 A1 | 5/2003 | Sugiura et al. |
| 6,993,371 B2 | 1/2006 | Kiani et al. | | 2003/0132495 A1 | 7/2003 | Mills et al. |
| 6,993,372 B2 | 1/2006 | Fine et al. | | 2003/0135099 A1 | 7/2003 | Al-Ali |
| 6,996,427 B2 | 2/2006 | Ali et al. | | 2003/0162414 A1 | 8/2003 | Schulz et al. |
| 7,003,338 B2 | 2/2006 | Weber et al. | | 2003/0171662 A1 | 9/2003 | O'Connor et al. |
| 7,003,339 B2 | 2/2006 | Diab et al. | | 2003/0176776 A1 | 9/2003 | Huiku |
| 7,005,573 B2 * | 2/2006 | Lionetta et al. ............ 174/387 | | 2003/0181799 A1 | 9/2003 | Lindekugel et al. |
| 7,006,855 B1 | 2/2006 | Sarussi | | 2003/0187337 A1 | 10/2003 | Tarassenko et al. |
| 7,006,856 B2 | 2/2006 | Baker, Jr. et al. | | 2003/0195402 A1 | 10/2003 | Fein et al. |
| 7,016,715 B2 | 3/2006 | Stetson | | 2003/0197679 A1 | 10/2003 | Ali et al. |
| 7,020,507 B2 | 3/2006 | Scharf et al. | | 2003/0212316 A1 | 11/2003 | Leiden et al. |
| 7,024,233 B2 | 4/2006 | Ali et al. | | 2003/0225323 A1 | 12/2003 | Kiani et al. |
| 7,024,235 B2 | 4/2006 | Melker et al. | | 2003/0225337 A1 | 12/2003 | Scharf et al. |
| 7,025,728 B2 | 4/2006 | Ito et al. | | 2003/0236452 A1 | 12/2003 | Melker et al. |
| 7,027,849 B2 | 4/2006 | Al-Ali et al. | | 2003/0236647 A1 | 12/2003 | Yoon et al. |
| 7,027,850 B2 | 4/2006 | Wasserman | | 2004/0006261 A1 | 1/2004 | Swedlow et al. |
| 7,035,697 B1 | 4/2006 | Brown | | 2004/0010188 A1 | 1/2004 | Wasserman et al. |
| 7,039,449 B2 | 5/2006 | Al-Ali | | 2004/0024297 A1 | 2/2004 | Chen et al. |
| 7,043,289 B2 | 5/2006 | Fine et al. | | 2004/0024326 A1 | 2/2004 | Yeo et al. |
| 7,047,055 B2 | 5/2006 | Boaz et al. | | 2004/0034293 A1 | 2/2004 | Kimball |
| 7,047,056 B2 | 5/2006 | Hannula et al. | | 2004/0039272 A1 | 2/2004 | Abdul-Hafiz et al. |
| 7,060,035 B2 | 6/2006 | Wasserman et al. | | 2004/0039273 A1 | 2/2004 | Terry |
| 7,062,307 B2 | 6/2006 | Norris et al. | | 2004/0054269 A1 | 3/2004 | Rantala et al. |
| 7,067,893 B2 | 6/2006 | Mills et al. | | 2004/0054291 A1 | 3/2004 | Schulz et al. |
| 7,072,701 B2 | 7/2006 | Chen et al. | | 2004/0059209 A1 | 3/2004 | Al-Ali et al. |
| 7,072,702 B2 | 7/2006 | Edgar, Jr. et al. | | 2004/0059210 A1 | 3/2004 | Stetson |
| 7,079,086 B2 * | 7/2006 | Aisenbrey ............... 343/872 | | 2004/0064020 A1 | 4/2004 | Diab et al. |
| 7,079,880 B2 | 7/2006 | Stetson | | 2004/0068164 A1 | 4/2004 | Diab et al. |
| 7,085,597 B2 | 8/2006 | Fein et al. | | 2004/0087846 A1 | 5/2004 | Wasserman |
| 7,096,052 B2 | 8/2006 | Mason et al. | | 2004/0089929 A1 * | 5/2004 | Chiu et al. .............. 257/678 |
| 7,096,054 B2 | 8/2006 | Abdul-Hafiz et al. | | 2004/0092805 A1 | 5/2004 | Yarita |
| 7,107,088 B2 | 9/2006 | Aceti | | 2004/0097797 A1 | 5/2004 | Porges et al. |
| 7,113,815 B2 | 9/2006 | O'Neil et al. | | 2004/0098009 A1 | 5/2004 | Boecker et al. |
| 7,123,950 B2 | 10/2006 | Mannheimer | | 2004/0107065 A1 | 6/2004 | Al-Ali et al. |
| 7,127,278 B2 | 10/2006 | Melker et al. | | 2004/0116788 A1 | 6/2004 | Chernoguz et al. |
| 7,130,671 B2 | 10/2006 | Baker, Jr. et al. | | 2004/0116789 A1 | 6/2004 | Boaz et al. |
| 7,132,641 B2 | 11/2006 | Schulz et al. | | 2004/0117891 A1 | 6/2004 | Hannula et al. |
| 7,133,711 B2 | 11/2006 | Chernoguz et al. | | 2004/0122300 A1 | 6/2004 | Boas et al. |
| 7,139,599 B2 | 11/2006 | Terry | | 2004/0122302 A1 | 6/2004 | Mason et al. |
| 7,142,901 B2 | 11/2006 | Kiani et al. | | 2004/0133087 A1 | 7/2004 | Ali et al. |
| 7,162,288 B2 | 1/2007 | Nordstrom | | 2004/0133088 A1 | 7/2004 | Al-Ali et al. |
| 7,190,987 B2 | 3/2007 | Lindekugel et al. | | 2004/0138538 A1 | 7/2004 | Stetson |
| 7,198,778 B2 | 4/2007 | Achilefu et al. | | 2004/0138540 A1 | 7/2004 | Baker, Jr. et al. |
| 7,209,775 B2 | 4/2007 | Bae et al. | | 2004/0143172 A1 | 7/2004 | Fudge et al. |
| 7,215,984 B2 | 5/2007 | Diab et al. | | 2004/0147821 A1 | 7/2004 | Al-Ali et al. |
| 7,225,006 B2 | 5/2007 | Al-Ali et al. | | 2004/0147822 A1 | 7/2004 | Al-Ali et al. |
| 7,232,988 B2 * | 6/2007 | Hamilton et al. ............ 250/239 | | 2004/0147823 A1 | 7/2004 | Kiani et al. |
| 7,236,811 B2 | 6/2007 | Schmitt | | 2004/0147824 A1 | 7/2004 | Diab et al. |
| 7,248,910 B2 | 7/2007 | Li et al. | | 2004/0152965 A1 | 8/2004 | Diab et al. |
| 7,254,433 B2 | 8/2007 | Diab et al. | | 2004/0158134 A1 | 8/2004 | Diab et al. |
| 7,254,434 B2 | 8/2007 | Schulz et al. | | 2004/0158135 A1 | 8/2004 | Baker, Jr. et al. |
| 7,263,395 B2 | 8/2007 | Chan et al. | | 2004/0162472 A1 | 8/2004 | Berson et al. |
| 7,272,426 B2 | 9/2007 | Scmid | | 2004/0171920 A1 | 9/2004 | Mannheimer et al. |

| | | | |
|---|---|---|---|
| 2004/0171948 A1 | 9/2004 | Terry | |
| 2004/0176671 A1 | 9/2004 | Fine et al. | |
| 2004/0181133 A1 | 9/2004 | Al-Ali | |
| 2004/0181134 A1 | 9/2004 | Baker, Jr. et al. | |
| 2004/0186358 A1 | 9/2004 | Chernow et al. | |
| 2004/0199063 A1 | 10/2004 | O'Neil et al. | |
| 2004/0204636 A1 | 10/2004 | Diab et al. | |
| 2004/0204637 A1 | 10/2004 | Diab et al. | |
| 2004/0204638 A1 | 10/2004 | Diab et al. | |
| 2004/0204639 A1 | 10/2004 | Casciani et al. | |
| 2004/0204865 A1 | 10/2004 | Lee et al. | |
| 2004/0210146 A1 | 10/2004 | Diab et al. | |
| 2004/0215069 A1 | 10/2004 | Mannheimer | |
| 2004/0230107 A1 | 11/2004 | Asada et al. | |
| 2004/0230108 A1 | 11/2004 | Melker et al. | |
| 2004/0236196 A1 | 11/2004 | Diab et al. | |
| 2004/0239578 A1* | 12/2004 | Aisenbrey | 343/872 |
| 2004/0242980 A1 | 12/2004 | Kiani et al. | |
| 2004/0249252 A1 | 12/2004 | Fine et al. | |
| 2004/0257557 A1 | 12/2004 | Block et al. | |
| 2004/0260161 A1 | 12/2004 | Melker et al. | |
| 2004/0267103 A1 | 12/2004 | Li et al. | |
| 2004/0267104 A1 | 12/2004 | Hannula et al. | |
| 2004/0267140 A1 | 12/2004 | Ito et al. | |
| 2005/0001780 A1* | 1/2005 | Aisenbrey | 343/873 |
| 2005/0004479 A1 | 1/2005 | Townsend et al. | |
| 2005/0046046 A1* | 3/2005 | Chiu et al. | 257/787 |
| 2005/0213871 A1* | 9/2005 | Schwiebert et al. | 385/14 |
| 2005/0253057 A1* | 11/2005 | Hamilton et al. | 250/239 |
| 2006/0084852 A1 | 4/2006 | Mason et al. | |
| 2006/0089547 A1 | 4/2006 | Sarussi | |
| 2006/0106294 A1 | 5/2006 | Maser et al. | |
| 2006/0195028 A1 | 8/2006 | Hannula et al. | |
| 2006/0224058 A1 | 10/2006 | Mannheimer | |
| 2006/0247501 A1 | 11/2006 | Ali | |
| 2006/0258921 A1 | 11/2006 | Addison et al. | |
| 2007/0032709 A1 | 2/2007 | Coakley et al. | |
| 2007/0032710 A1 | 2/2007 | Raridan et al. | |
| 2007/0032715 A1 | 2/2007 | Eghbal et al. | |
| 2007/0073126 A1 | 3/2007 | Raridan, Jr. | |
| 2007/0078311 A1 | 4/2007 | Al-Ali et al. | |
| 2008/0117616 A1* | 5/2008 | Coakley | 361/818 |
| 2008/0118736 A1* | 5/2008 | Drzal et al. | 428/297.4 |
| 2008/0272469 A1* | 11/2008 | Kwak et al. | 257/659 |
| 2008/0281014 A1* | 11/2008 | Momose et al. | 522/71 |
| 2008/0304246 A1* | 12/2008 | Utschig et al. | 361/818 |
| 2008/0315371 A1* | 12/2008 | Tang et al. | 257/659 |
| 2009/0323267 A1* | 12/2009 | Besko et al. | 361/679.4 |
| 2010/0020518 A1* | 1/2010 | Bustamante | 361/818 |
| 2010/0044840 A1* | 2/2010 | Tang et al. | 257/659 |
| 2010/0065788 A1* | 3/2010 | Momose et al. | 252/511 |

FOREIGN PATENT DOCUMENTS

| | | |
|---|---|---|
| DE | 3703458 | 8/1988 |
| DE | 19632361 | 2/1997 |
| DE | 19640807 | 9/1997 |
| EP | 0127947 | 12/1984 |
| EP | 0531631 | 3/1993 |
| EP | 0724860 | 8/1996 |
| EP | 1491135 | 12/2004 |
| FR | 2685865 | 7/1993 |
| JP | 2111343 | 4/1990 |
| JP | 3116259 | 5/1991 |
| JP | 3116260 | 5/1991 |
| JP | 3245042 | 10/1991 |
| JP | 5049625 | 3/1993 |
| JP | 6014906 | 1/1994 |
| JP | 6269430 | 9/1994 |
| JP | 7001273 | 1/1995 |
| JP | 7136150 | 5/1995 |
| JP | 7236625 | 9/1995 |
| JP | 10216115 | 8/1998 |
| JP | 10337282 | 12/1998 |
| JP | 2000237170 | 9/2000 |
| JP | 2004159810 | 6/2004 |
| JP | 2004248820 | 9/2004 |
| JP | 2004261364 | 9/2004 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9001293 | 2/1990 |
| WO | WO9111137 | 8/1991 |
| WO | WO9309711 | 5/1993 |
| WO | WO9502358 | 1/1995 |
| WO | WO9736536 | 10/1997 |
| WO | WO9857577 | 12/1998 |
| WO | WO9947039 | 9/1999 |
| WO | WO0059374 | 10/2000 |
| WO | WO0117421 | 3/2001 |
| WO | WO2005010567 | 2/2005 |
| WO | WO2005010568 | 2/2005 |

OTHER PUBLICATIONS

Izumi, Akio, et al.; "Accuracy and Utility of a New Reflectance Pulse Oximeter for Fetal Monitoring During Labor," Journal of Clinical Monitoring, vol. 13, pp. 103-108 (1997).

"Smaller Product, Tighter Tolerances Pose Dispensing Challenges for Medical Device Manufacturer," Adhesives Age, pp. 40-41 (Oct. 1997).

Crilly, Paul B., et al.; "An Integrated Pulse Oximeter System for Telemedicine Applications," IEEE Instrumentation and Measurement Technology Conference, Ottawa, Canada; May 19-21, 1997; pp. 102-104.

DeKock, Marc; "Pulse Oximetry Probe Adhesive Disks: a Potential for Infant Aspiration," Anesthesiology, vol. 89, pp. 1603-1604 (1998).

Rhee, Sokwoo, et al.; "The Ring Sensor: a New Ambulatory Wearable Sensor for Twenty-Four Hour Patient Monitoring," Proceedings of the 20th annual International Conference of the IEEE Engineering in Medicine and Biology Society, vol. 20, No. 4, pp. 1906-1919.

Yang, Boo-Ho, et al.; "A Twenty-Four Hour Tele-Nursing System Using a Ring Sensor," Proceedings of the 1998 IEEE International Conference on Robotics & Automation, Leaven, Belgium, May 1998; pp. 387-392.

Such, Hans Olaf; "Optoelectronic Non-invasive Vascular Diagnostics Using multiple Wavelength and Imaging Approach," Dissertation, (1998).

Ferrell, T.L., et al.; "Medical Telesensors," SPIE, vol. 3253, pp. 193-198 (1998).

Ikeda, Kenji, et al.; "Improvement of Photo-Electric Plethysmograph Applying Newly Developed Opto-Electronic Devices," IEEE Tencon, pp. 1109-1112 (1999).

Yang, Boo-Ho, et al.; "Development of the ring sensor for healthcare automation," Robotics and Autonomous Systems, vol. 30, pp. 273-281 (2000).

Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," Proceedings of the 22nd Annual EMBS International Conference, Chicago, Illinois; Jul. 23-28, 2000; pp. 2796.

Schulz, Christian Eric; "Design of a Pulse Oximetry Sensor Housing Assembly," California State University Master's Thesis, UMI Dissertation Services, UMI No. 1401306, (May 2000) 63 pages.

Aoyagi, T., et al.; "Pulse Oximeters: background, present and future," Neonatal Care, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," Journal of the Japanese Society of Emergency Medicine, Kanto Region, vol. 21, pp. 26-27 (2000) (Article in Japanese—contains English summary.

Gisiger, P.A., et al.; "OxiCarbo®, a single sensor for the non-invasive measurement of arterial oxygen saturation and CO2 partial pressure at the ear lobe," Sensor and Actuators, vol. B-76, pp. 527-530 (2001).

Cysewska-Sobusaik, Anna; "Metrological Problems With noninvasive Transillumination of Living Tissues," Proceedings of SPIE, vol. 4515, pp. 15-24 (2001).

Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).

Lopez-Sliva, Sonnia Maria Lopez, et al.; "NIR transmittance pulse oximetry system with laser diodes," Clinical Diagnostic Systems, Proceedings of SPIE, vol. 4255, pp. 80-87 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Tobata, H., et al.; "Study of Ambient Light Affecting Pulse Oximeter Probes," Ikigaku (Medical Technology), vol. 71, No. 10, pp. 475-476 (2002) (Article in Japanese—contains English summary of article).

Irie, A., et al.; "Respiration Monitors—Pulse Oximeters," Neonatal Care, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," IEEE, pp. 193-194 (2002).

Warren, Steve, et al.; "Wearable Sensors and Component-Based Design for Home Health Care," Proceedings of the Second Joint EMBS/BMES Conference, Houston, Texas; Oct. 23-26, 2002; pp. 1871-1872.

Cyrill, D., et al.; "Adaptive Comb Filter for Quasi-Periodic Physiologic Signals," Proceedings of the 25th Annual International Conference of the IEE EMBS, Cancun, Mexico, Sep. 17-21, 2003; pp. 2439-2442.

Aoyagi, Takuo; "Pulse oximetry: its invention, theory, and future," Journal of Anesthesia, vol. 17, pp. 259-266 (2003).

Itoh, K., et al.; "Pulse Oximeter," Toyaku Zasshi (Toyaku Journal), vol. 25, No. 8, pp. 50-54 (2003) (Article in Japanese—contains English summary of article).

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Johnston William S., et al.; "Effects of Motion Artifacts on helmet-Mounted Pulse Oximeter Sensors," 2 pgs. (2004).

Matsuzawa, Y., et al.; "Pulse Oximeter," Home Care Medicine, pp. 42-45 (Jul. 2004); (Article in Japanese—contains English summary of article).

Urquhart, C., et al.; "Ear probe pulse oximeters and neonates," Anaesthesia, vol. 60, p. 294 (2005).

Odagiri, Y.; "Pulse Wave Measuring Device," Micromechatronics, vol. 42, No. 3, pp. 6-11 (undated) (Article in Japanese—contains English summary of article).

Bentley, David J. et al.; "Measure Pressure with Thin Film"; Paper Film & Foil Converter; May 1, 2003.

http://www.fcw.com.my/fujifilm.html.

* cited by examiner

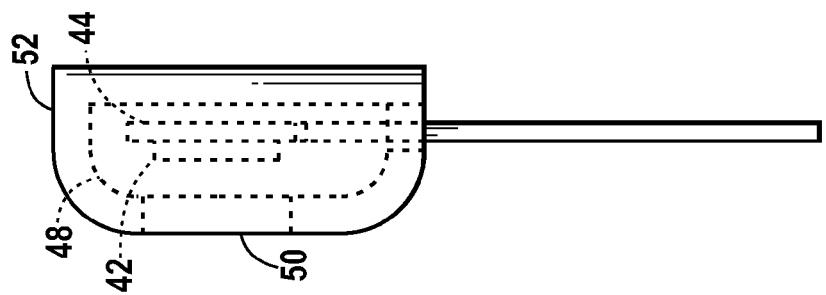
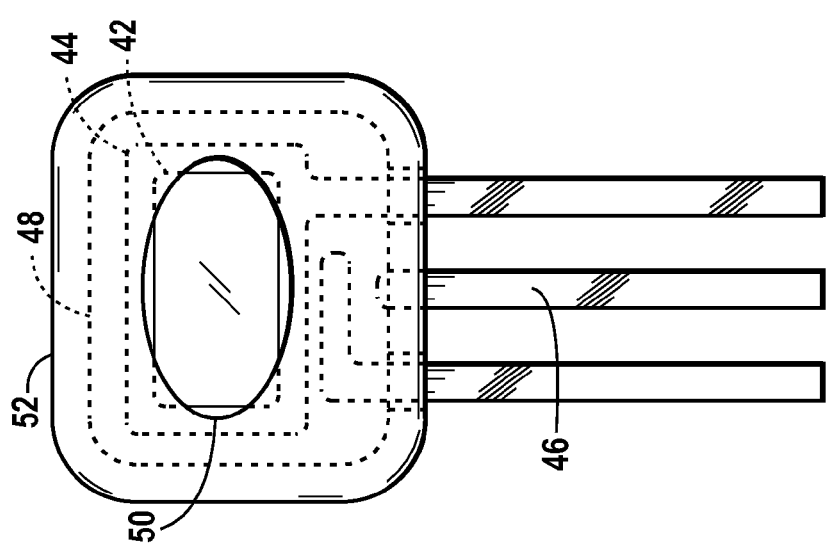
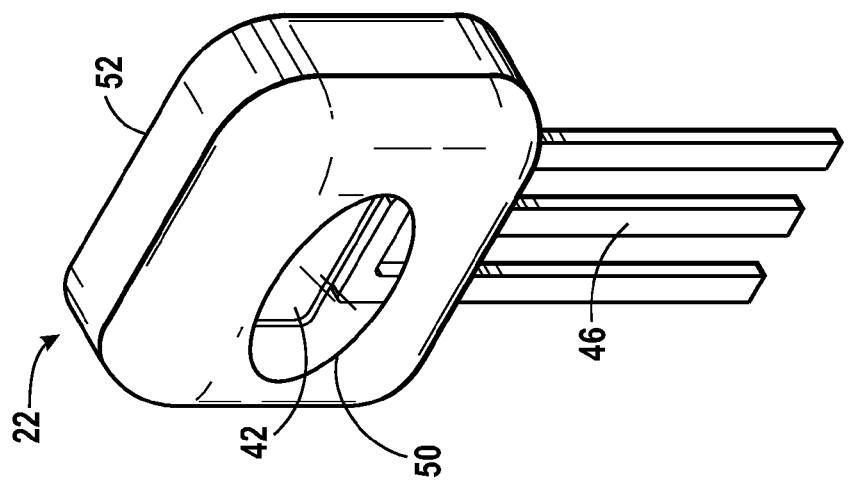

OPTICAL DETECTOR WITH AN OVERMOLDED FARADAY SHIELD

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices and techniques have been developed for monitoring physiological characteristics. Such devices and techniques provide doctors and other healthcare personnel with the information they need to provide the best possible healthcare for their patients. As a result, these monitoring devices and techniques have become an indispensable part of modern medicine.

One such monitoring technique is commonly referred to as pulse oximetry. Pulse oximetry may be used to measure various blood flow characteristics, such as the blood-oxygen saturation of hemoglobin in arterial blood and/or the rate of blood pulsations corresponding to each heartbeat of a patient.

The devices based upon pulse oximetry techniques are commonly referred to as pulse oximeters. Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. A photo-plethysmographic waveform, which corresponds to the cyclic attenuation of optical energy through the patient's tissue, may be generated from the detected light. Additionally, one or more physiological characteristics may be calculated based upon the amount of light absorbed or scattered. More specifically, the light passed through the tissue may be selected to be of one or more wavelengths that may be absorbed or scattered by the blood in an amount correlative to the amount of a blood constituent, such as oxygen or oxyhemaglobin, present in the blood. The amount of light absorbed and/or scattered may then be used to estimate the amount of oxygen in the tissue using various algorithms.

For example, a reflectance-type sensor placed on a patient's forehead may emit light into the skin and detect the light that is "reflected" back after being transmitted through the forehead tissue. A transmission-type sensor may be placed on a finger, wherein the light waves are emitted through and detected on the opposite side of a finger. In either case, the amount of light detected may provide information that corresponds to valuable physiological patient data. The data collected by the sensor may be used to calculate one or more of the above physiological characteristics based upon the absorption or scattering of the light. For instance, the emitted light is typically selected to be of one or more wavelengths that are absorbed or scattered in an amount related to the presence of oxygenated versus de-oxygenated hemoglobin in the blood. The amount of light absorbed and/or scattered may be used to estimate the amount of the oxygen in the tissue using various algorithms.

The sensors generally include an emitter that emits the light and a detector that detects the light. The emitter and detector may be located on a flexible circuit that allows the sensor to conform to the appropriate site on the patient's skin, thereby making the procedure more comfortable for a patient. During use, the emitter and detector may be held against the patient's skin to facilitate the light being directed into and received from the skin of the patient. For example, a sensor may be clipped about a patient's finger tip with the emitter placed against the finger nail, and the detector placed against the under side of the finger tip. When fitted to the patient, the emitted light may travel directly through the tissue of the finger and be detected without additional light being introduced or the emitted light being scattered.

However, in practice, the shape and design of the sensor may be uncomfortable to the patient. Discomfort may be caused by shielding and protection provided on the optical devices, i.e. the photodetector and the emitter. For example, the detector and emitter may include materials or layers to protect measurement signals from being affected by external static electrical fields or external light. These materials can add to the bulkiness of the sensor. Further, after repeated use, the materials and layers may separate or delaminate, causing additional discomfort and resulting in potential erroneous measurements. Moreover, manufacturing the sensor, the optical devices and the protective layers may be a tedious and time consuming activity.

BRIEF DESCRIPTION OF THE DRAWINGS

Advantages of the disclosure may become apparent upon reading the following detailed description and upon reference to the drawings in which:

FIGS. 8A-8C are views of the photodetector assembly shown in FIGS. 1-5, shown after the application of a nonconductive transparent overmold and a conductive overmold, in accordance with an embodiment.

DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described herein, various embodiments of sensors are provided featuring various coatings to prevent shunting and interference from external light as well as external static forces. Further the embodiments of sensors discussed are designed to fit a range of patient application areas and are designed to provide a simplified method for manufacturing. In general, embodiments of the sensors include optical components (e.g., emitters and detectors) that are coated with a material that blocks the passage of light from external sources as well as directly between the emitter and detector. In certain embodiments, one or more of the optical components may also be coated with a material that prevents or reduces electrical interference.

Figure 1:
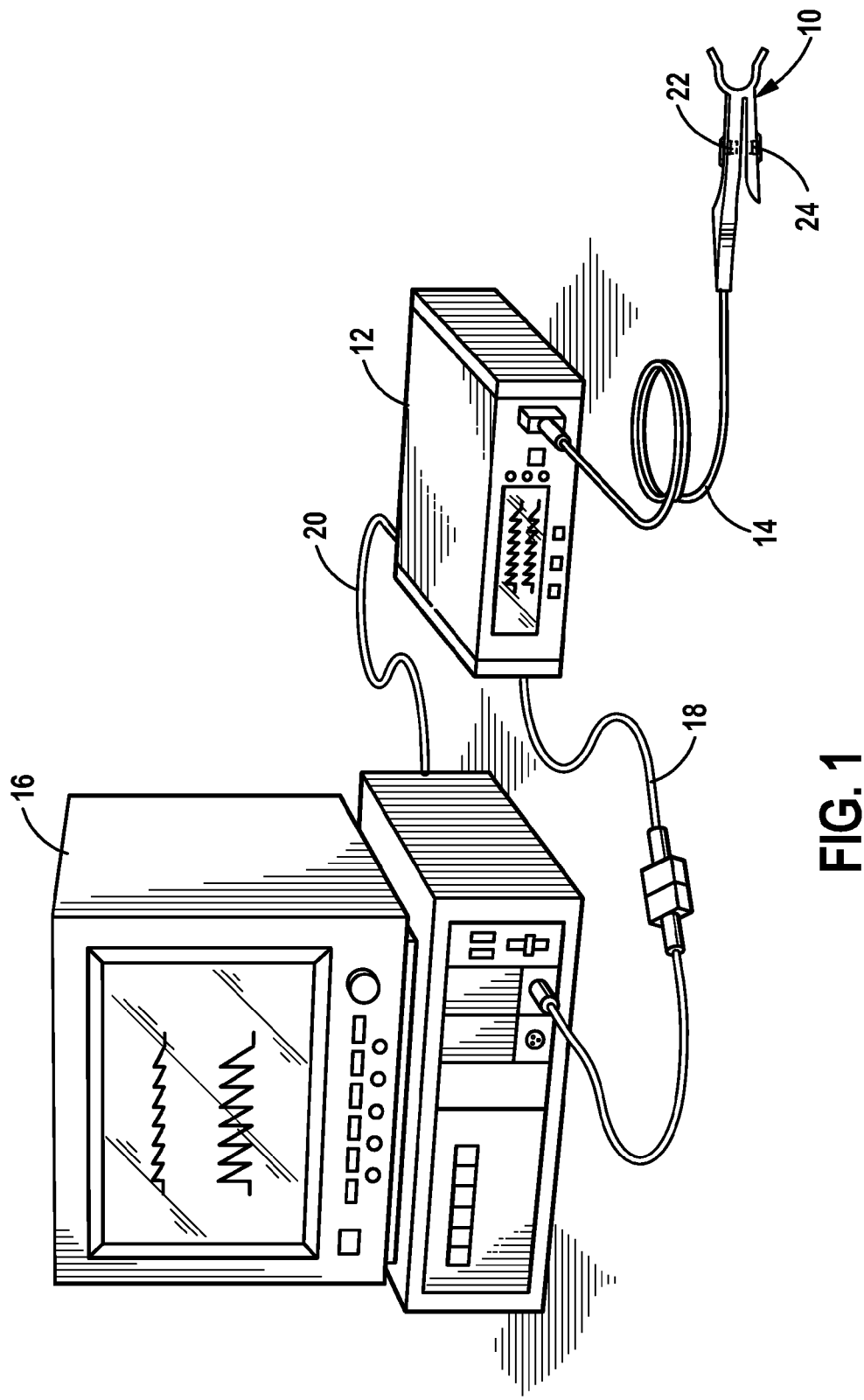
FIG. 1 illustrates a patient monitoring system coupled to a multi-parameter patient monitor and a sensor assembly including a photodetector, in accordance with an embodiment.

Prior to discussing examples of such sensor assemblies in detail, it should be appreciated that such sensors may be typically designed for use with a patient monitoring system. For example, referring now to FIG. 1, sensor 10 may be used in conjunction with patient monitor 12. Sensor 10, as depicted in FIG. 1, is designed to be placed on a patient's finger. In the depicted embodiment, cable 14 connects sensor 10 to patient monitor 12. Sensor 10 and/or cable 14 may include or incorporate one or more integrated circuit or electrical devices, such as a memory processor chip, that may facilitate or enhance communication between sensor 10 and patient monitor 12. Similarly, cable 14 may be an adaptor cable, with or without an integrated circuit or electrical device, for facilitating communication between sensor 10 and various types of monitors, including different versions of patient monitor 12 or other physiological monitors. In other embodiments, sensor 10 and patient monitor 12 may communicate via wireless means such as using radio frequency, infrared, or optical signals. In such embodiments, a transmission device may be connected to sensor 10 to facilitate wireless transmission between sensor 10 and patient monitor 12. As will be appreciated by those of ordinary skill in the art, cable 14 (or a corresponding wireless connection) may be used to transmit control or timing signals from patient monitor 12 to sensor 10 and/or to transmit acquired data from sensor 10 to patient monitor 12.

In one embodiment, patient monitor 12 may be a suitable pulse oximeter, such as those available from Nellcor Puritan Bennett L.L.C. In other embodiments, patient monitor 12 may be a monitor suitable for measuring tissue water fractions, or other body fluid related metrics, using spectrophotometric or other techniques. Furthermore, patient monitor 12 may be a multipurpose monitor suitable for performing pulse oximetry and measurement of tissue water fraction, or other combinations of physiological and/or biochemical monitoring processes, using data acquired via the sensor 10 and/or other sensors. Moreover, to upgrade conventional monitoring functions provided by the system, patient monitor 12 may be coupled to a multi-parameter patient monitor 16 via cable 18 connected to a sensor input port and/or a cable connected to a digital communication port.

In an embodiment, the sensor 10, as depicted in FIG. 1, may be a clip-style sensor assembly. In such an embodiment, the clip-style sensor may utilize transmission spectrophotometric techniques to monitor one or more parameters. In other embodiments, the sensor 10 may be a reflectance type sensor assembly using reflectance spectrophotometric techniques. The sensor 10 may include optical components, such as detector 22 and emitter 24, which may be of any suitable type. For example, in one embodiment the emitter 24 may be one or more light emitting diodes adapted to transmit one or more wavelengths of light, such as in the red to infrared range, and the detector 22 may be a photodetector, such as a silicon photodiode package, selected to receive light in the range emitted from the emitter 24. In the present context, detector 22 may be referred to as a photodetector, a detector device, a detector assembly or a detector component. Further, detector 22 and emitter 24 may be referred to as optical components or devices.

In the depicted embodiment, the sensor 10 is coupled to a cable 14 that is responsible for transmitting electrical and/or optical signals to and from the emitter 24 and the detector 22 of the sensor 10. The cable 14 may be permanently coupled to the sensor 10, or it may be removably coupled to the sensor 10—the latter alternative being more useful and cost efficient in situations where the sensor 10 is disposable. In an embodiment where sensor 10 is disposable, the unitary assemblies of emitter 24 and detector 22 as described herein may allow them to be easily removed from the sensor body, which may be disposed of after use on a patient. The emitter 24 and detector 22 may then be cleaned and placed in a new sensor body for use on a new patient.

Figure 2:
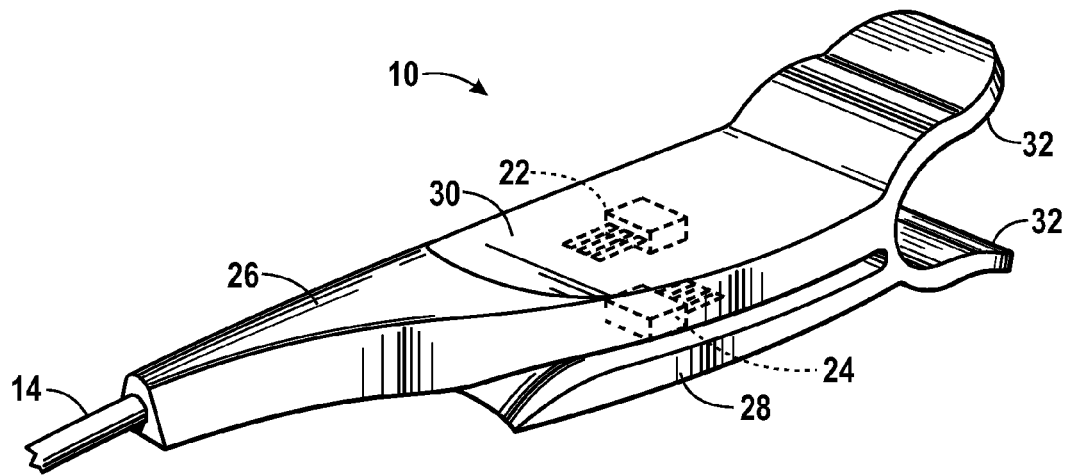
FIG. 2 is a perspective view of a clip style embodiment of the sensor assembly shown in FIG. 1, in accordance with an embodiment, mounted in the hat.

Turning now to FIG. 2, a perspective view of a clip-style embodiment of sensor 10 is shown, according to an embodiment. The assembly of sensor 10 includes an upper clip portion 26 and a lower clip portion 28. As depicted, upper clip portion 26 includes a housing 30 that features a cavity for detector 22, while the lower clip portion 28 includes a cavity for emitter 24. In other embodiments the emitter 24 and detector 26 may be reversed. Further, housing 30 may be configured to allow detector 22 to be removed either through the outer portion of housing 30 or the skin contacting portion of upper clip portion 26. As depicted, the sensor assembly 10 may allow the optical devices to be easily removed for cleaning of the sensor body and the devices. Further, the components and/or sensor body may be covered with an overmold that would facilitate cleaning, such as by rinsing off the device or body with water or a solution.

Figure 3:
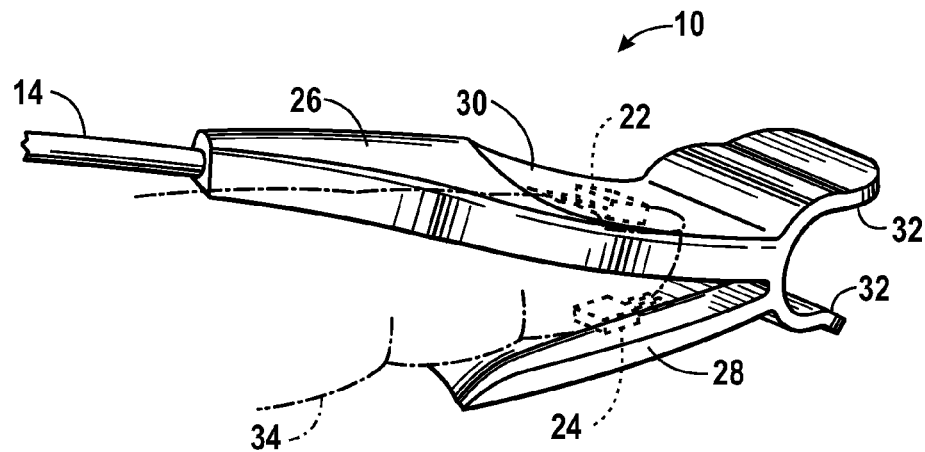
FIG. 3 is a perspective view of the sensor assembly shown in FIG. 1 placed on a patient's finger, in accordance with an embodiment.

FIG. 3 shows the clip-style embodiment of sensor assembly 10 in operation. As depicted, upper clip portion 26 and lower clip portion 28 have been separated, allowing a patient's finger 34 to be inserted in the clip-style sensor assembly 10. In one embodiment, light waves may be emitted by emitter 24 into the bottom of patient finger 34. The light waves may then be transmitted through the patient's finger tissue and received by detector 22. A signal corresponding to the detected light waves may be sent to the patient monitor via cable 14. In one embodiment, the skin contacting components of sensor assembly 10 may be formed to be as comfortable as possible so as not to irritate the skin while the sensor is on a patient's finger. Therefore, utilizing suitable materials for sensor assembly 10 improves overall comfort and performance of clip style sensor assembly 10.

Figure 4:
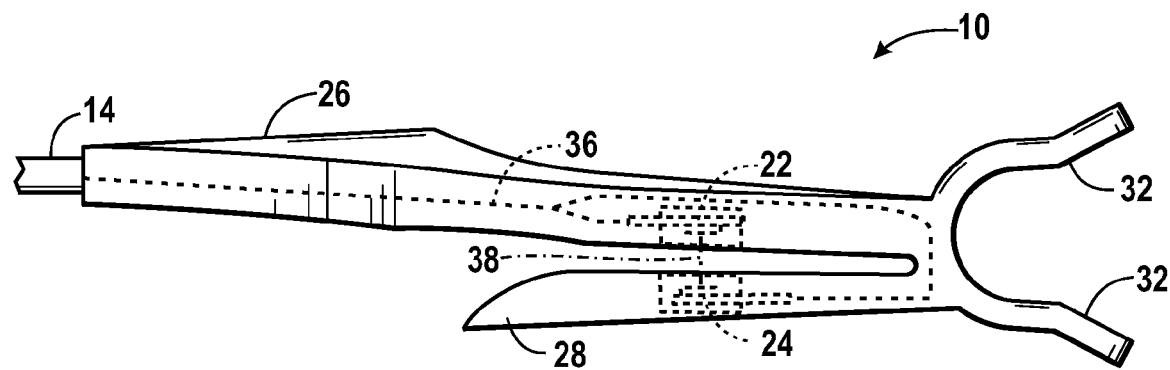
FIG. 4 is a side view of the sensor assembly shown in FIG. 1, including a photodetector and an emitter, in accordance with an embodiment.

With the foregoing discussion in mind and turning now to FIG. 4, a cut-away side view of a clip-style embodiment of sensor assembly 10 is illustrated. In one embodiment, detector device 22 may be located on the skin contacting side of upper clip portion 26. Similarly, emitter device 24 may be located on the skin contacting side of lower clip portion 28. Signals may be routed to or from the optical devices by component lead wires 36 which may be bundled into cable 14. Detector device 22 and emitter device 24 may each include or be proximate to a transparent window which allows light to be transmitted between the optical components via light transmission path 38, which may pass through a patient's finger tissue.

Figure 5:
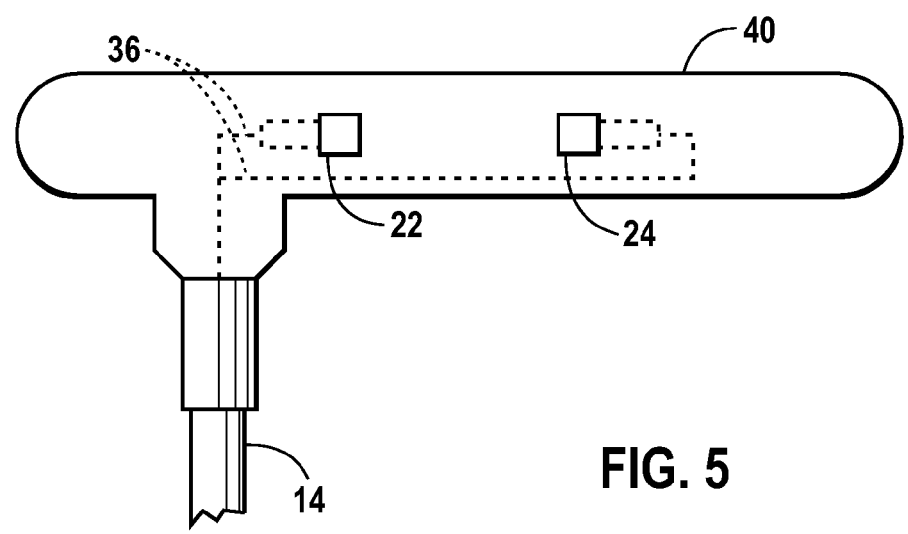
FIG. 5 illustrates a view of a bandage style embodiment of the sensor assembly, in accordance with an embodiment.

In other embodiments, the sensor may not be a clip-style sensor. For example, turning now to FIG. 5, an embodiment of a bandage style sensor 40 is illustrated. The bandage style sensor 40 may be applied to any well perfused area of a patient, such as a patient's forehead. As depicted, the bandage style sensor 40 may include optical devices photodetector 22 and emitter 24. In one embodiment, the optical devices each feature windows that allow light to be transmitted to and received from the patient's tissue. In one embodiment, signals may be transmitted to and from the optical devices by lead wires 36. In the depicted embodiment, lead wires 36 route signals to the monitor via cable 14. In one embodiment, the bandage style sensor 40 may use an adhesive layer to attach the sensor 40 to the patient's skin. The adhesive layer may include an acrylic or synthetic rubber adhesive or other suitable adhesives. Alternatively, in another embodiment, the bandage style sensor 40 may be applied without adhesive, instead being made from a foam PVC or foam polyurethane material and attached to the skin by medical tape.

Figure 6C:
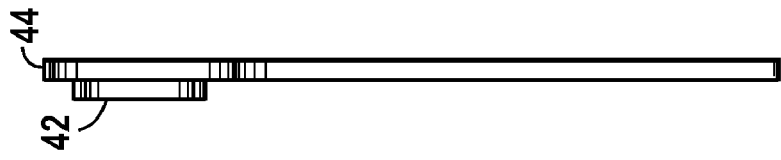
FIG. 6A-6C are views of the photodetector assembly shown in FIGS. 1-5, shown prior to application of overmolds, in accordance with an embodiment.
Figure 6B:
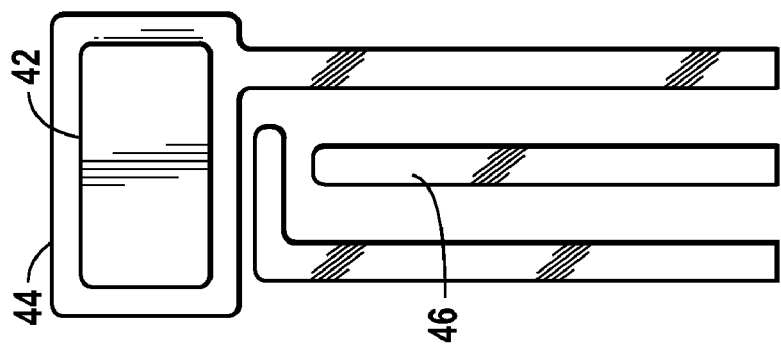
Figure 6A:
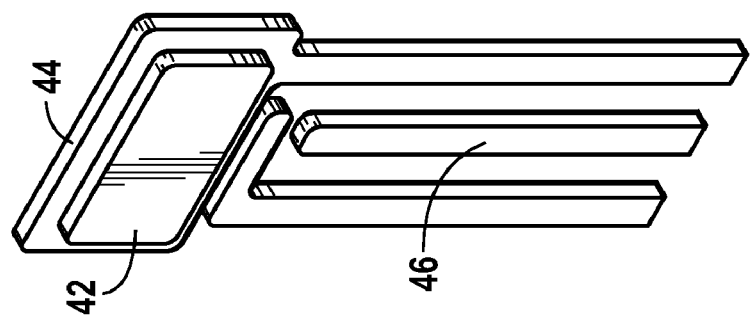
Figure 7C:
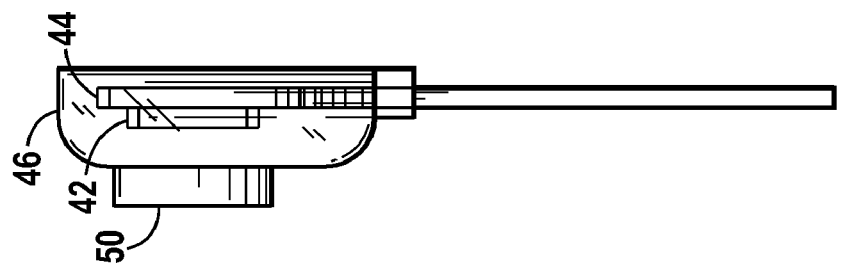
FIG. 7A-7C are views of the photodetector assembly shown in FIGS. 1-5, shown after the application of a nonconductive transparent overmold, in accordance with an embodiment.
Figure 7B:
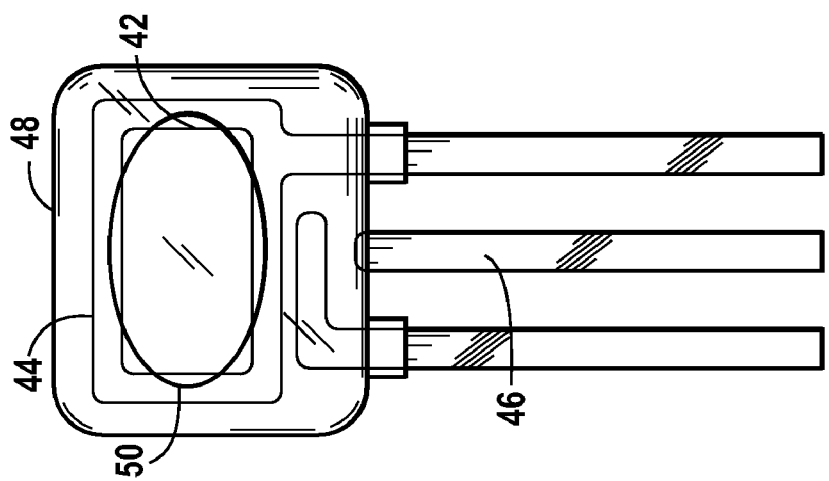
Figure 7A:
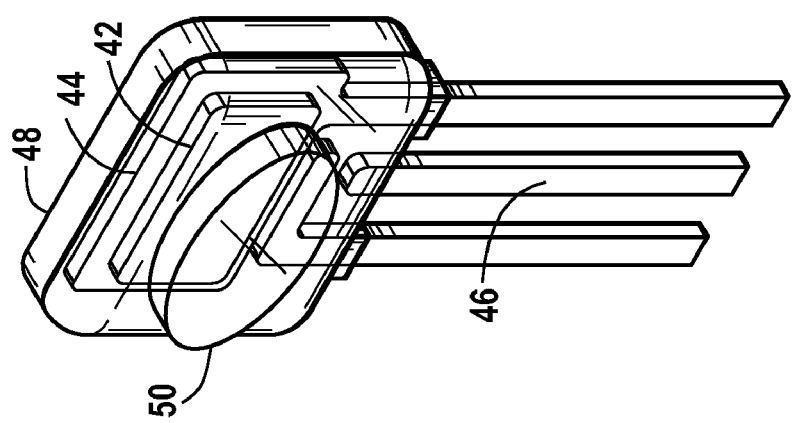

With the foregoing discussion of various sensor and optical component assemblies in mind, FIGS. 6A through 8C show embodiments of a photodetector assembly for use in accordance with the present disclosure. In particular, FIGS. 6A through 8C show various stages of one embodiment of a manufacturing process for the photodetector assembly. FIGS. 6A-6C show perspective, front and side views of the photodetector assembly prior to the application of overmold materials. In the depicted embodiment, the photodetector assembly includes detector face 42, lead frame 44, and ground lead 46. In one embodiment, detector face 42 receives light waves that are converted into electrical signals which are transmitted to an associated patient monitor via lead frame 44 and attached cables. FIG. 7A-7C illustrates the photodetector assembly after the application of an overmold material, in accordance with an embodiment. For example, in one such embodiment, the photodetector assembly includes transparent non-conductive overmold 48 disposed about detector face 42 and a portion of lead frame 44. In the depicted embodiment, the transparent non-conductive overmold 48 includes a protruding window 50. In one such embodiment, window 50 is located in front of detector face 42, thereby permitting light to be received by the detector face 42 through the window 50.

FIGS. 8A-8C show perspective, front and side views of a photodetector assembly after the application of transparent non-conductive overmold 48 and conductive overmold 52, in accordance with an embodiment. In one embodiment, the conductive overmold 52 may cover a portion of lead frame 44 and transparent non-conductive overmold 48. In the depicted embodiment, conductive overmold 52 does not cover window 50 which allows detector face 42 to receive incoming light waves. Further, in the depicted embodiment, conductive overmold 52 is approximately the same thickness as the protrusion of window 50, meaning that the surface of conductive overmold 52 is flush with the surface of window 50. In one embodiment, ground lead 46 is in contact with conductive overmold 52, enabling the conductive overmold 52 to be connected via cable to a ground located on a monitor.

In one embodiment, a substantial portion of the photodetector assembly is shielded from electromagnetic and static fields by conductive overmold 52, which serves as a Faraday shield for the optical device. In one such embodiment, transparent non-conductive overmold 48 insulates detector face 42 and other assembly components from electrical contact with conductive overmold 52. Transparent non-conductive overmold 48 and conductive overmold 52 may be composed of any suitable material, such as neoprene, silicone, plastic, polyurethane, polypropylene, nylon, urethane, epoxy, and/or other suitable materials. Moreover, different materials or combinations of materials may be used for each of the overmolds. For instance, in one embodiment, the conductive overmold 52 may be composed of a medical grade silicone, epoxy, and/or polypropylene containing a conductive additive, such as metal fibers, carbon fibers, carbon powders or carbon nanotubes. In one embodiment, conductive overmold 52 may be completely or partially opaque, however, in other embodiments, conductive overmold 52 is not opaque.

In one embodiment, the optical component and associated overmold layers constitute an assembly that may be inserted and removed from the sensor body. For example, in one embodiment, a photodetector assembly, as shown in FIGS. 6A-8C, may be utilized in a suitable pulse oximetry sensor, including the bandage-style sensor of FIG. 5 or the clip-style sensor of FIGS. 1-4. In addition, the arrangement of the overmold layers in such an embodiment protects the photodetector device from contaminants and other debris by providing a hermetic seal about the components.

In certain embodiments, the use of overmolded optical components also allows a simplified approach to cleaning and replacing the optical components within a sensor assembly. For example, in one embodiment the photodetector assembly may be removed as an integral unit from a housing or frame of a clip style sensor by application of a mechanical force to overcome a force that may be exerted by the housing to keep the assembly in place. As described herein, in certain embodiments the photodetector assembly may include a cable connected to the lead frame 44 and covered in a rubber casing, which, along with the overmolds, provide protection for the entire detector assembly. In one such embodiment, the rubber casing and overmold allow the assembly to be easily cleaned with water or a solution. After removal of such an overmolded detector assembly, the housing may also be easily cleaned. Similarly, the easy removal and insertion of the detector assembly allows for simplified replacement of the device in the sensor housing.

The application of transparent nonconductive overmold 48 and/or conductive overmold 52 to the optical components, such as the photodetector, may be accomplished by any suitable means. For example, in one embodiment, a detector assembly may be formed by an injection molding process. In one example of such a process the lead frame 44 and detector 22 may be positioned within a die or mold of the desired shape for the assembly. A molten or otherwise unset overmold material may then be injected into the die or mold. For example, in one implementation, a molten thermoplastic elastomer at between about 400° F. to about 450° F. is injected into the mold. The overmold material may then be set, such as by cooling for one or more minutes or by chemical treatment, to form the overmold layer about the lead frame 44 and detector 22. Further, the application of an overmold, as described herein, may be applied to any suitable electronic component, including LEDs and photodiodes.

The configuration, thickness, and number of overmold layers may vary depending upon several factors including size and weight constraints as well as costs, materials used, manufacturing limitations and environment. In one embodiment, the use of one or two overmold layers may reduce the complexity of the detector assembly, thereby reducing overall size and bulkiness of the photodetector assembly. For example, the use of conductive overmolding instead of metallic mesh for the device's Faraday shield may be more compact, resist separation/delamination and eliminate a source of discomfort for the patient. In other embodiments, additional overmold layers, such as an addition nonconductive overmold layer may be utilized. Further, the simplified approach to shielding the photodetector may increase robustness of the photodetector and sensor assembly by providing an overmolded material that will resist delamination or degradation after repeated use. Moreover, the assembly may allow for easy removal of the unitary optical device, thereby enabling the device to be removed and replaced for cleaning or maintenance. The arrangement also allows for a simplified manufacturing process for the optical device, thereby reducing costs and complexity of the sensor assembly.

While the disclosure may be susceptible to various modifications and alternative forms, specific embodiments have been shown by way of example in the drawings and have been described in detail herein. However, it should be understood that the disclosure is not intended to be limited to the particular forms provided. Rather, the disclosure is to cover all modifications, equivalents, and alternatives falling within the spirit and scope of the disclosure as defined by the following appended claims. Indeed, the present disclosed methods may not only be applied to transmission type sensors for use in pulse oximetry, but also to other sensor designs. Likewise, the present disclosure is not limited to use on ears, digits, or foreheads but may also be applied to placement on other body parts.

What is claimed is:

1. A photoelectric sensor assembly, comprising:
   an emitter adapted to transmit one or more wavelengths of light;
   a photodetector adapted to receive the one or more wavelengths of light emitted by the emitter; and
   a sensor body configured to receive the emitter and the photodetector, wherein a nonconductive overmold is disposed over the photodetector but not the emitter and the sensor body and a conductive overmold is disposed about all or part of the nonconductive layer.

2. The assembly of claim 1, wherein the conductive overmold is adapted to shield at least a portion of the photodetector from electromagnetic and static fields.

3. The assembly of claim 1, wherein the nonconductive overmold comprises a transparent material.

4. The assembly of claim 1, wherein the nonconductive overmold comprises a neoprene, a silicone, a plastic, an epoxy, or a polyurethane, or any combination thereof.

5. The assembly of claim 1, wherein the conductive overmold comprises a substantially opaque material.

6. The assembly of claim 1, wherein the conductive overmold comprises a silicone, a neoprene, a nylon, a plastic, an epoxy, or a polyurethane and one or more conductive additives, or a combination thereof.

7. The assembly of claim 1, wherein the nonconductive overmold comprises a protrusion that includes an outer surface that is substantially flush with the outer surface of the conductive overmold, wherein the protrusion is located above an active face of the electronic device.

8. An assembly, comprising:
   an emitter adapted to transmit one or more wavelengths of light;
   a photodetector adapted to receive the one or more wavelengths of light emitted by the emitter;
   a sensor body configured to receive the emitter and the photodetector; and
   wherein a generally transparent nonconductive overmold is disposed over the photodetector but not the emitter and the sensor body, a conductive overmold is disposed about a portion of the transparent nonconductive overmold, and a second nonconductive overmold is disposed over the sensor body.

9. The assembly of claim 8, wherein the transparent nonconductive overmold comprises a neoprene, a silicone, an epoxy, a plastic, or a polyurethane, or a combination thereof.

10. The assembly of claim 8, wherein the transparent nonconductive overmold comprises a protrusion that comprises an outer surface that is substantially flush with an outer surface of the conductive overmold.

11. The assembly of claim 8, wherein the conductive overmold comprises a medical grade silicone, a neoprene, a nylon, an epoxy, or a polyurethane and one or more conductive additives, or a combination thereof.

12. A method of manufacturing a photoelectric sensor assembly, comprising:
    providing an emitter adapted to transmit one or more wavelengths of light;
    providing a photodetector adapted to receive the one or more wavelengths of light; and
    providing a sensor body configured to receive the emitter and the photodetector, wherein a nonconductive overmold is provided over the photodetector but not the emitter and the sensor body and a conductive overmold is provided about all or part of the nonconductive layer.

13. The method of claim 12, wherein the nonconductive material comprises a neoprene, a silicone, a plastic, or a polyurethane, or a combination thereof.

14. The method of claim 12, wherein the sensor body comprises a clip-style sensor assembly body or a bandage style sensor body.

15. The method of claim 12, wherein the conductive material comprises a medical grade a silicone, a neoprene, a plastic, an epoxy, or a polyurethane and a conductive additive, or a combination thereof.

16. The assembly of claim 1, wherein the photodetector comprises a unitary assembly removable from the sensor body for reuse in an alternate sensor body.

17. The method of claim 12, wherein the photodetector comprises a unitary assembly removable from the sensor body for reuse in an alternate sensor body.

* * * * *